United States Patent [19]

Sigl et al.

[11] 4,213,459
[45] Jul. 22, 1980

[54] DISPOSABLE DIAPER WITH LOCALIZED AREA OF INCREASED DENSITY

[75] Inventors: Wayne C. Sigl, Black Creek; Philip A. LaBorde, Appleton, both of Wis.

[73] Assignee: Kimberly-Clark Corporation, Neenah, Wis.

[21] Appl. No.: 905,384

[22] Filed: May 12, 1978

Related U.S. Application Data

[63] Continuation of Ser. No. 736,944, Oct. 29, 1976, abandoned.

[51] Int. Cl.² ............................................. A61F 13/16
[52] U.S. Cl. .................................................... 128/287
[58] Field of Search .............................. 128/284, 287

[56] References Cited

U.S. PATENT DOCUMENTS

| | | | |
|---|---|---|---|
| 3,592,194 | 7/1971 | Duncan | 128/287 |
| 3,603,314 | 9/1974 | Aberg | 128/284 |
| 3,769,978 | 11/1973 | DeNight et al. | 128/287 |
| 3,881,490 | 5/1975 | Whitehead et al. | 128/290 R |
| 3,965,904 | 6/1976 | Mesek et al. | 128/287 |
| 4,027,672 | 6/1977 | Karami | 128/287 |

*Primary Examiner*—Robert W. Michell
*Assistant Examiner*—C. W. Shedd
*Attorney, Agent, or Firm*—William D. Herrick; Howard Olevsky

[57] ABSTRACT

A disposable diaper in which the main absorbent pad is a fluff batt having a specially selected localized area of increased density to improve the effective fluid absorbing capabilities of the diaper when worn, and to minimize waist leakage problems. The localized area of increased density is longitudinally centered in the back panel at the upper rear section of the diaper as worn, and extends from the waist of the diaper to the approximate transverse midpoint of the diaper. This densified area is also spaced inwardly from the side edges of the diaper to leave sections of undensified fluff along each side.

3 Claims, 3 Drawing Figures

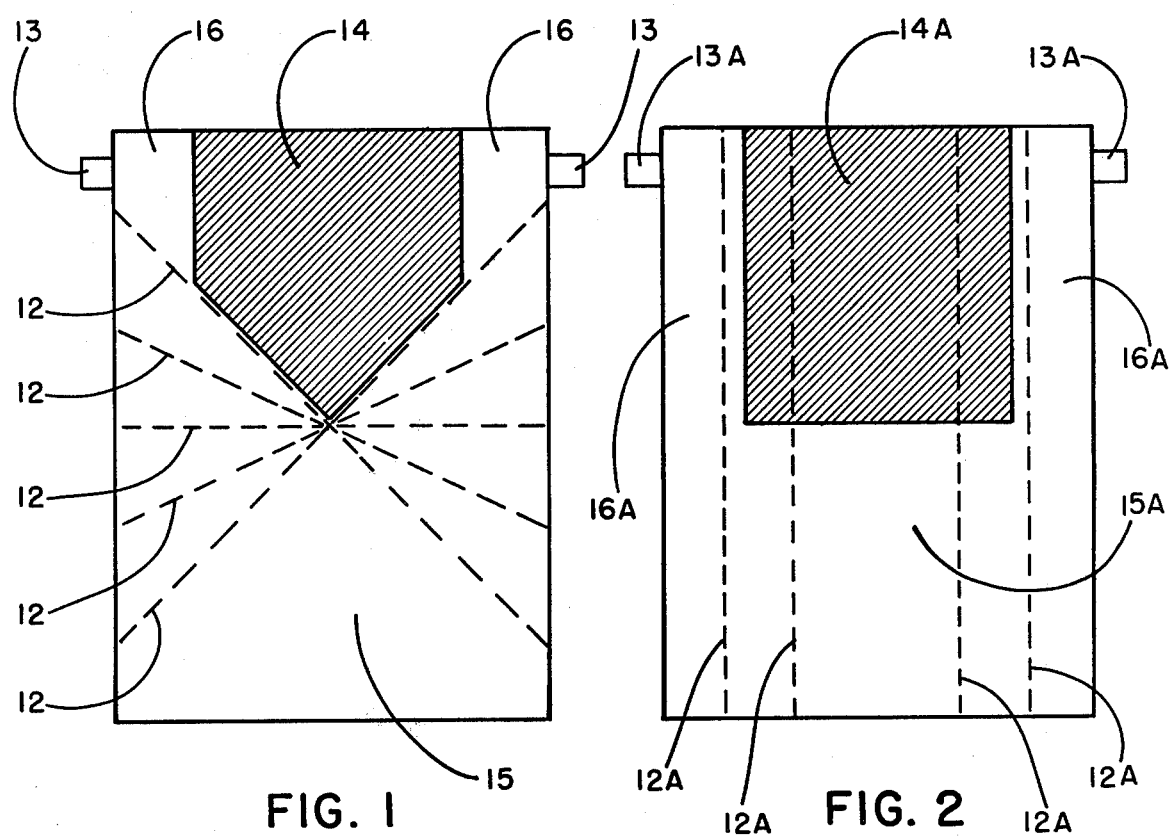
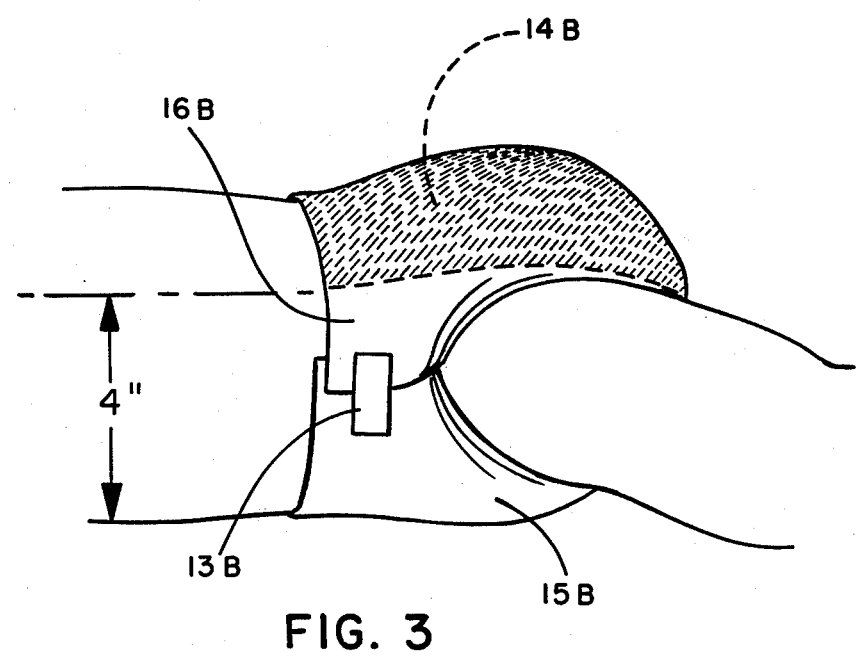

DISPOSABLE DIAPER WITH LOCALIZED AREA OF INCREASED DENSITY

This is a continuation of application Ser. No. 736,944, filed Oct. 29, 1976 now abandoned.

BACKGROUND OF THE INVENTION

In the art of disposable diapers the most practical material for use as the main absorbent pad element from a unit cost standpoint is an air-formed fluff batt of cellulosic wood fibers. The majority of disposable diapers now being marketed employ such elements. Batts made from these fibers have a low density and a high capacity for fluid absorption but have very poor wicking ability. As a result the areas which become wetted by absorbed fluid in an unmodified fluff batt during use are basically controlled by gravity and are relatively small with respect to total area available leaving much potential capacity unused. Generally speaking, the areas of greatest fluid acceptance and therefore the most efficient with respect to utilization of potential absorbent capacity are the areas of an absorbent fluff batt closest to the point of initial wetting, or at the lowest position of the structure in use in relation to gravity flow. In other words, as batt areas become farther removed from the initial point of wetting and/or are located at higher positions in relation to gravity flow from the point of wetting during use they become less efficient with respect to utilization of potential absorbent capacity.

It is well known that the wicking ability of a fluff batt, as well as other types of fibrous batts, is improved by increasing its density through the use of overall compression, line embossing, pattern embossing, or the like whereby pore sizes in the densified batt area are reduced, thereby increasing capillary suction pressure to such extent that absorbed fluids will overcome the force of gravity sufficiently to be capable of moving into the densified areas from the less dense areas. One of the first to recognize this phenomenon was Heitmeyer in U.S. Pat. No. 1,863,333. More recent variations are found in Morin 2,788,003; Burgeni 2,952,259-60; Gobbo Sr. et al 3,065,751; Bletzinger et al 3,375,827; Murphy 3,430,629; Krusko 3,766,922; and DeNight et al 3,769,978. As indicated in these patents, it is also known that while capillarity is improved by densification which reduces average pore size, the total fluid receiving capacity of a fluff batt is decreased as the average pore size is decreased. Thus, while the use of embossing or other means of densification does obtain better distribution of fluid within a fluff or other fibrous batt it does so with some loss in capacity and is at best a compromise, i.e., a trade-off of better distribution of fluid throughout the available area for a decrease in total capacity for the same area. In most cases the advantages of using more of the available area tends to overshadow slightly the loss of capacity and is usually the design of choice. In instances such as in U.S. Pat. No. 3,769,978, where line-embossing is utilized to improve distribution, larger quantities of fluff are placed in the area where initial wetting takes place and where maximum capacity is most needed in order to make up for loss in capacity which results from the embossing. While this construction improves fluid distribution it does so at an added material cost which is undesirable from an economic standpoint.

Applicant has now found how to structure a diaper to achieve distribution of absorbed fluid into those areas of the diaper where distribution has been lacking or poor during use, and thereby effectively utilize most of the available capacity in those areas, without at the same time reducing potential capacity where distribution is already optimum during use and without requiring the use of additional absorbent material.

The present invention is therefore directed to a structure designed to use the fluid absorbent capacity of a fluff batt in those areas which because of poor flow characteristics were hitherto substantially inaccessible to fluids and therefore unused, such areas being in a location farthest removed from the initial wetting point and/or in a location highest in relation to gravity flow from the wetting point. In the structure disclosed, there is no impairment or reduction in the absorbent capacity of the more efficient areas of the diaper which are located at or near the initial point of wetting and which are positioned lowest in relation to gravity flow from that initial point of wetting. This improved capability is accomplished by retaining that part of the batt which has a high efficiency with respect to absorption properties in its relatively undensified condition while selectively densifying only that portion of the batt which, when not densified as defined herein, is generally not wetted in use. This structure increases capillary pressures in the hitherto unused areas to an extent that fluid will be drawn out of the less dense area even against the influence of gravity.

SUMMARY OF THE INVENTION

This invention is directed to an improvement in the structure of a disposable diaper of the type which is generally comprised of an air-formed fluff batt sandwiched between a fluid-permeable body-contacting web and a fluid-impermeable backing sheet.

The improvement consists in densifying a selected area of the fluff batt to improve its ability to draw absorbed fluid therein from other fluid-receiving parts of the diaper, while leaving these other parts of the diaper substantially undensified.

The selected area of increased density is longitudinally centered in the back panel of the diaper as worn, starting at the approximate transverse centerline of the diaper and extending to the waist. The densified area is also preferably spaced inwardly from the side edges of the diaper in the back panel, leaving the side portions of the back panel undensified along with the entire front panel.

When a diaper of this construction is placed on an infant and the infant assumes a stomach down sleeping or resting position, the densified portion will generally be located at a distance in the range of 4" to 5" above the plane in contact with the infant.

Other features, objects and advantages of the invention will become apparent by reference to the accompanying drawings and the detailed description which follows.

BRIEF DESCRIPTION OF THE DRAWINGS

In the drawings:

FIG. 1 is a plan view of a diaper in accordance with the invention.

FIG. 2 is a plan view of another embodiment of the diaper.

FIG. 3 is a partial side view, showing the configuration a diaper of this invention takes on the body of an infant in prone position.

DETAILED DESCRIPTION OF PREFERRED EMBODIMENTS

Before describing the preferred embodiments some additional discussion relating to the development of the improved efficiency diaper as defined herein appears appropriate.

The basic aim of a diapering garment of course, is to receive and absorb all fluid and solid discharges from the perineal area and to retain the discharged material within the garment without leakage—all this to be accomplished with minimum discomfort to the child and minimum inconvenience to the mother.

In examining used diapers which had leaked in use, to determine how the fluid is distributed in the absorbent pad, it was found that most of the fluid was confined to the front panel area of the diaper as worn, while the rear panel was relatively dry and unused. The front panel was also found to be substantially soaked and near or beyond its absorbent capacity. It was further found that a large percentage of the leakage as reported by users, occurred at the front waist, particularly in very young infants and when the diaper was worn overnight. Very few leaks were found to occur while the child was in an upright sitting or standing position.

Further study also found that most infants sleep on their stomachs, or in a prone position. From these observations it appeared that one could minimize the leakage problem by adding more absorbent material to the front panel and the central portions of the diaper. Evidence of this is found in the many patents which emphasize putting extra absorbent material where the action is. While such modification did reduce leakage incidents, it was not considered practical or satisfactory, because the additional amount of absorbent material which was needed for the purpose increased product costs and because the added bulk resulted in a poor fit which detracted from both comfort and appearance. In addition, there was no improvement in the utilization of the already available absorbent capacity in the rear panel section.

In order to utilize the latter while maintaining a good fit and appearance, attempts were then made to improve capillarity which could serve to draw fluid into this unused panel section by embossing the diaper over its entire length. This embossing provided capillary channels throughout the diaper and did obtain better overall distribution. However, this structure also reduced the overall capacity of the diaper while having no discernible effect on reducing waist leakage. In some cases, in fact, the latter situation appeared to be aggravated.

It was then discovered that the overall performance of a diaper with respect to efficient use of available absorbent capacity could be markedly improved by densifying only a selected area of the back panel section of the diaper, as defined in this invention, without adding additional absorbent material in the front panel. While such improved performance is obtained when the entire rear half of the diaper is densified, best results are obtained if only the longitudinal center portion from the rear waist to the transverse midpoint of the diaper is densified leaving the rear panel edges undensified, this latter being the preferred embodiment.

In FIGS. 1 and 2 there are shown two variations of the preferred embodiment. FIG. 1 represents a plan view of a disposable diaper in accordance with this invention and of the general type described in Hrubecky U.S. Pat. No. 3,196,874 which relates to a disposable diaper provided with a plurality of triangular inpleats formed along fold lines 12. In its folded condition this style of diaper has a generally triangular configuration with a downwardly depending pocket at the intersection of the lines as described in the patent. The structural components of the diaper comprise the conventional air-formed cellulosic fluff absorbent pad sandwiched between a fluid-pervious cover sheet and a fluid-impervious back sheet of plastic film or the like. Pressure-sensitive fastening tapes 13 may be secured at the two rear corners as shown. In the FIG. 1 embodiment of this invention, the shaded area 14 of the back panel is compressed and the fluff batt densified to a density of about 0.09 gm/cc. The remaining unshaded areas 15, 16 represents the undensified fluff batt area having a density of about 0.05 gm/cc.

The five-sided shape of densified area 14 is provided in this style diaper only because it conveniently fits into the triangular format. The densified area may of course take various other shapes, the important consideration being that the densified area be transversely centered in the back panel of the diaper and extend from the border of the diaper at the rear waist area to the transverse centerline of the diaper.

It is preferred that longitudinal edge areas of the back panel also remain undensified along with the entire front panel, but some of the advantages of the improved structure are achieved even if these edge areas are also densified.

In FIG. 2 there is shown an embodiment of the invention as adapted to wing-fold diapers, which are also well known in the art, and are prefolded along parallel longitudinal fold lines 20 to form box pleats on each side. In this embodiment the densified area 14a is still located in the central rear panel, but is in the form of a rectangle extending from the transverse center line to the rear waist border. This configuration is more appropriate for use with wing-fold style diapers.

In both embodiments, the diaper when in position on an infant, and when the infant is lying on its stomach, will appear approximately as shown in FIG. 3. This figure shows a side view of a portion of a child's body in a prone position which is the most common reclining position for young infants. As indicated here, the densified portion of the diaper, shaded area 14b, is disposed in the highest position with respect to the plane on which the child is resting. The edge of the densified area then is found to be at a distance of about 4" to 5" above that plane depending on the size of the child.

In such position, body discharge, and particularly urine, first strikes the diaper in the undensified portion 15b and is diffused throughout that portion largely by lateral flow and gravity. It has been found that absorbed fluid will also flow upward in a fluff sheet to a minor extent for a distance of about 4" from the plane on which the child rests and will sometimes go as high as 5" above the plane depending upon how the fluff is compacted during use. In the improved diaper, capillary suction pressure provided by densified area 14b will then take over and pull fluids into densified section 14b, thus utilizing the back panel area which in the absence of densification otherwise remains dry and unused.

It is well known that diaper wetting by infants is periodic and in gushes. As a result it usually takes several wettings before leaking diapers are detected. With the improved structure, undensified section 15b apparently is capable of handling the initial gushes and then between discharges permits some of the fluid to be drawn up into densified area 14b, this intermittent flow and redistribution thus permits the absorbent capacity of 15b to be restored to some extent. Accordingly, in the improved diaper a larger number of fluid discharges can be accepted before leakage occurs as compared to an unmodified diaper. That is, in the absence of a densified rear panel section 14b, there is no transfer of fluid from undensified area 15b and waist leakage occurs sooner.

The preferred type of densification of the rear panel section is one which is uniform over the entire densified area, such as may be accomplished for example by uniformly compressing this area through use of a flat plate and high pressure. Various line pattern embossments as are found in overall embossing used for fluid control in prior art structures may also be employed but these are not as efficient as a uniformly densified panel.

The preferred densities of the fluff batt in the described construction is about 0.05 gm/cc in the undensified areas and 0.09 gm/cc in the densified area. Densities may of course, vary from these preferred figures and still take advantage of the improvements defined herein. It should be noted that in the manufacturing process, a fluff batt because of its tenuous nature is generally debulked to some extent as it passes through nips during handling. Accordingly the term undensified as used herein means a batt which has been debulked as little as possible. In any event the undensified area is always less compacted than the densified area. The important consideration is that the densified area have a higher capillary suction pressure than the undensified area. Care should be taken that the undensified area not be debulked too much from pressures applied in the manufacturing process in order to avoid needless reduction in capacity. While the specific densities noted above are preferred for best performance, a workable range is about from 0.07 gm/cc to 0.25 gm/cc in the densified area and 0.02 gm/cc to 0.07 gm/cc in the undensified area.

What is claimed is:

1. In a disposable diaper of the type having a fluff batt as its main absorbent element and in which said diaper and said batt are defined by front and back waist-encircling ends, a pair of leg-encircling sides, a front panel section and a back panel section, the improvement wherein only a the improvement wherein only a localized contiguous area of the fluff batt in only the back panel section is comprised of a substantially uniformly deposited contiguous layer, said fluff layer of said localized area being comprised of a fluff having a substantially higher density than the density of the remainder of said back panel section and substantially higher than the density of the total whole of said front panel section, said localized area having a shape which consists of a transversely centered symetrical polygon, the number of sides in said polygon ranging from four to five, said localized area of higher density fluff comprising only the major central portion of said back panel section of the batt extending from the back waist end of the batt to the transverse mid-point of the batt, the remaining portions of the batt being undensified fluff which is in capillary association with said higher density fluff to permit unimpaired flow of fluids between said undensified fluff and said higher density fluff, said remaining portions of undensified fluff specifically including (a) the entire front panel section of the batt and (b) the two side areas of the back panel section of the batt; each of said side areas being of substantial width and extending alongside said area of higher density fluff from the front panel section of the batt to the back waist end of the batt.

2. The diaper of claim 1 wherein the localized area of higher density has a density in the range of about 0.07 gm/cc to about 0.25 gm/cc and the remainder of the diaper has a density of about 0.02 gm/cc to about 0.07 gm/cc.

3. The diaper of claim 1 wherein the localized area of higher density has a density of about 0.09 gm/cc and the remainder of the diaper has a density of about 0.05 gm/cc.

* * * * *